United States Patent [19]
Kubein-Meesenburg et al.

[11] Patent Number: 6,120,543
[45] Date of Patent: Sep. 19, 2000

[54] ARTIFICIAL JOINT, IN PARTICULAR ENDOPROSTHESIS FOR REPLACING NATURAL JOINTS

[75] Inventors: Dieter Kubein-Meesenburg, Kreiensen; Hans Nägerl, Klein-Lengden, both of Germany

[73] Assignee: Joachim Theusner, Germany

[21] Appl. No.: 08/981,028

[22] PCT Filed: Jun. 14, 1996

[86] PCT No.: PCT/EP96/02566

§ 371 Date: Feb. 17, 1998

§ 102(e) Date: Feb. 17, 1998

[87] PCT Pub. No.: WO97/00053

PCT Pub. Date: Jan. 3, 1997

[30] Foreign Application Priority Data

Jun. 14, 1995 [DE] Germany .......................... 195 21 597

[51] Int. Cl.[7] .................................. A61F 2/38; A61F 2/30
[52] U.S. Cl. ................................. 623/20; 623/18
[58] Field of Search .................. 623/20, 21, 23, 623/18

[56] References Cited

U.S. PATENT DOCUMENTS

| | | | |
|---|---|---|---|
| 3,748,662 | 7/1973 | Helfet | 623/20 |
| 3,798,679 | 3/1974 | Ewald | 623/20 |
| 4,242,759 | 1/1981 | White | 623/21 |
| 5,330,533 | 7/1994 | Walker | 623/20 |
| 5,556,432 | 9/1996 | Kubein-Meesenburg | 623/20 |

*Primary Examiner*—David H. Willse
*Attorney, Agent, or Firm*—Jones & Askew, LLP

[57] ABSTRACT

The present invention concerns an artificial joint, in particular an endoprosthesis to replace natural joints, consisting of at least two artificial joint parts with curved articulation surfaces, wherein, on each of the articulation surfaces, a contact line (k) in the shape of the arc of a circle is formed, which is a section of a contact circle with a center (M), lying in a plane. The articulation surfaces are arranged as a pair with respect to one another in such a manner that the contact lines (k) can roll onto one another, and vertical to the plane of the contact circles, are intersected at an intersection point (S) by axes (m) passing through their center (M). Ruled surfaces (3,4), formed from a large number of straight paths of contact (s), are partially formed on the contact lines (k), wherein the paths of contact lie on momentary connecting lines (s) of contact points (K), momentarily appearing during the rolling movement, with the momentary intersection points (S), which are produced by a swivel movement of the contact lines (k) with an angular velocity ($\Omega$) around a common tangent (t) of the contact lines (k) through the momentary contact points (K).

5 Claims, 8 Drawing Sheets

ARTIFICIAL JOINT, IN PARTICULAR ENDOPROSTHESIS FOR REPLACING NATURAL JOINTS

The present invention concerns an artificial joint, particularly an endoprosthesis for replacement of natural joints, consisting of at least two artificial joint parts, each with curved articulation surface, on which the joint parts articulate relative to one another.

Such an artificial joint is known from German Patent Application No. P 4202717.9. Here, the joint surfaces have planes vertical with respect to one another, a longitudinal plane and a transverse plane, different circular section contours, wherein the curvature ratios of the articulation surfaces in each of the planes are convex-convex, convex-concave, or concave-concave, and the joint geometry of the articulation surfaces with respect to one another, in each of the two planes, is determined by a joint chain with two joint axes (dimeric joint chain), which pass through the rotation centers of the articulation surface of the individual section contours. Since the articulation surfaces of this artificial joint are shaped convex-concave, concave-concave, or convex-convex, punctiform force transfer areas are formed, wherein increased surface pressing on the articulation surfaces arises, which can lead to material wear. In this way, the service life of these artificial joints can be shortened. In order to attain an improvement in force transfer between the articulation surfaces of the joint parts, the proposal is made that, in the known joint, a pressure distribution element be placed between these articulation surfaces, with which a better and more uniform force distribution is attained. These pressure distribution elements, however, increase the number of the required joint parts of the artificial joint.

The goal of the present invention is to create an artificial joint in which the punctiform force transfer areas are avoided and in which the incorporation of pressure distribution elements is not required, and which, at the same time, makes possible an optimal adaptation to the realities of the human body in use as an endoprosthesis for a natural human joint.

In accordance with the invention, this is attained with an artificial joint which consists of at least two artificial joint parts with curved articulation surfaces, wherein on each of the articulation surfaces, a contact line shaped as an arc of a circle is formed, which, in each case, is a section of a contact circle, lying in a plane with a center M, wherein the articulation surfaces are arranged as a pair with respect to one another in such a way that the contact lines can roll onto one another and axes running vertical to the plane and through the center of the contact circles intersect in an intersection point S, whereby ruled surfaces which are formed from a large number of straight pathlines of contact are found at one side of the contact lines, whereby the pathlines of contact lie on the momentary connecting lines of the momentary contact points, momentarily appearing during the rolling movement, with the momentary intersection points, which are produced by a swiveling movement of the contact lines at an angular velocity $\Omega$ around a common tangent of the contact lines through the momentary contact points. In accordance with the invention, therefore, a spatial gear system is formed. Here, a contact line is assigned to the individual joint surface of each joint part (limb), wherein these contact lines always touch and have a common contact tangent. During the articulation of the joint parts, the slope of the contact lines lying on the contact circles can be changed with respect to one another, wherein they carry out a rotation around the joint contact tangent moving in the contact point, so that then the contact circle axes exhibit a varying spherical arrangement with respect to one another. Since, in accordance with the invention, in the area of the ruled surfaces, straight pathlines of contact are present between the articulating ruled surfaces, wherein these pathlines of contact emanate from the contact point of the contact lines, an area of direct force transfer arises next to the contact lines, wherein line-shaped force transfer areas are formed by the pathlines of contact. Thus, a punctiform force transfer is avoided, wherein the material stress in the area of the ruled surfaces is substantially reduced in comparison to known joints. In this way, it is possible to use materials which are able to tolerate reduced loads. Kinematically, the joint in accordance with the invention, which is formed by the contact of the ruled surfaces with one another, has four degrees of freedom. This is true because with a fixed ruled surface of a joint part, the other ruled surface can glide along the common pathline of contact (first degree of freedom); it can glide from one touching line of contact to another pathline of contact (second degree of freedom); it can roll from one pathline of contact to the other pathline of contact (third degree of freedom); and it can rotate around a point on the momentarily common pathline of contact (fourth degree of freedom). The artificial joint in accordance with the invention is particularly suitable for an endoprosthetic knee joint, but also, in its basic design, for the articulation surfaces of the human elbow joint or the human ankle joint. In particular, if two of the joint parts arranged in pairs, in accordance with the invention, are designed parallel, joined into one joint, for example, for the creation of a human knee joint, a planar or spherical controlled movement of the limb coupled by the joint, with respect to one another, is attained.

On the basis of the embodiment examples depicted in the appended figures, the invention is explained in more detail.

Figure 1:
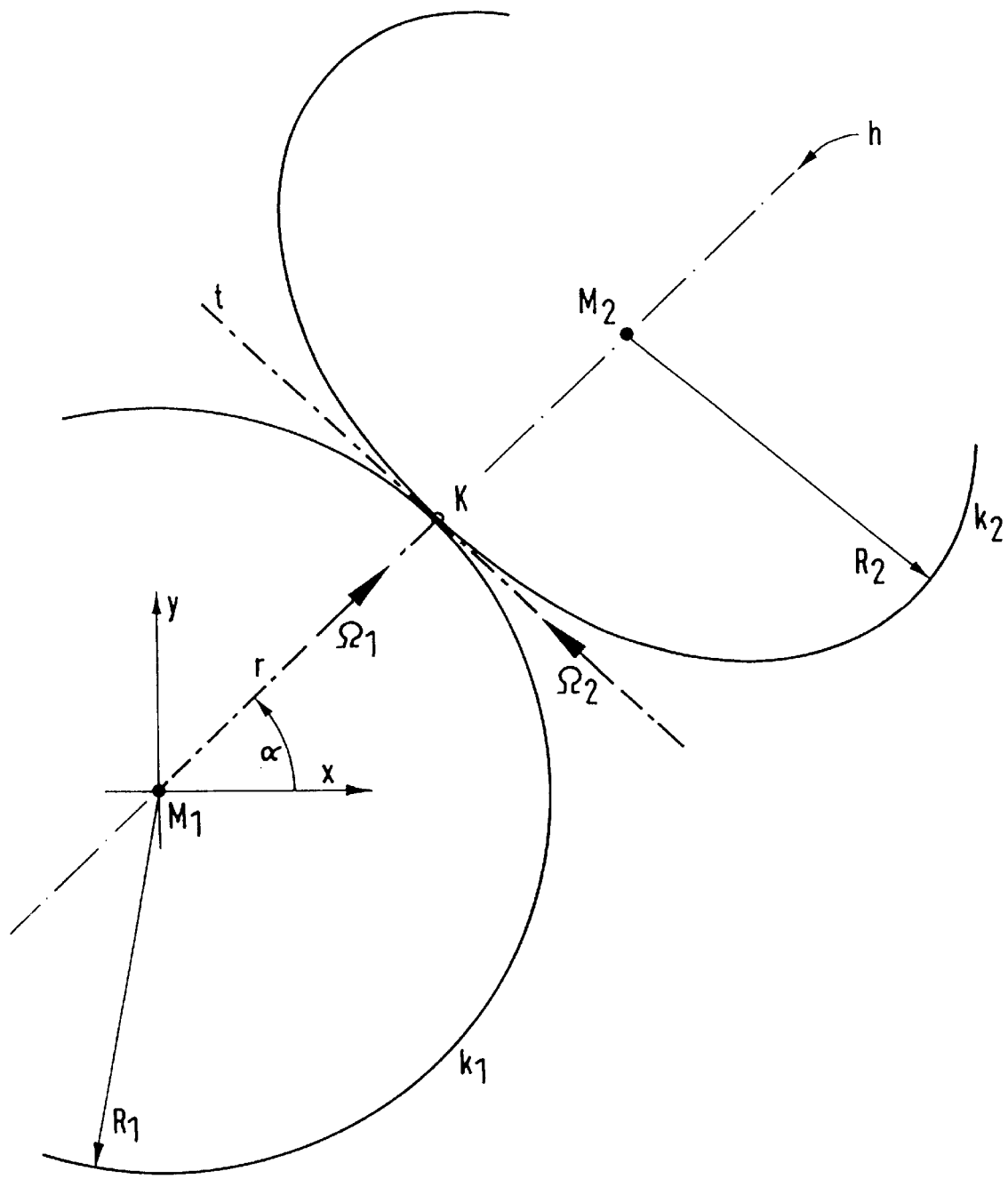
FIG. 1 shows a basic representation of the correlation of contact lines, lying on contact circles, with common contact tangents.
Figure 2:
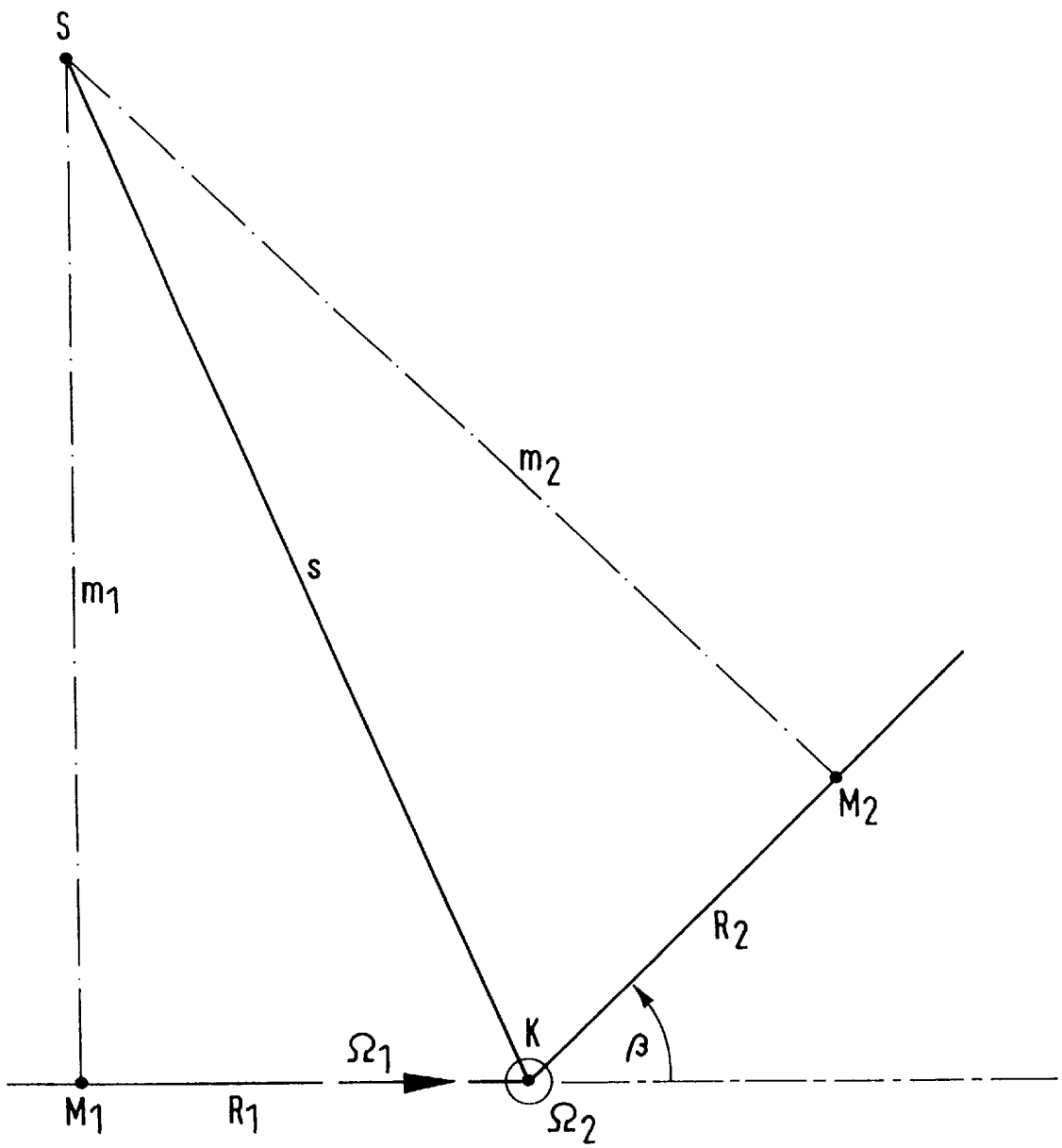
FIG. 2 shows a view according to FIG. 1 in the plane vertical to the planes of the contact circles.

The basic drawing shown in FIG. 1 depicts a contact line $k_1$ and a contact line $k_2$. These contact lines $k_1$ and $k_2$ are sections of contact circles with the center $M_1$ and the radius $R_1$ or the center $M_2$ and the radius $R_2$. These contact lines $k_1$ and $k_2$ are formed on articulation surfaces of a joint body 1 and a joint body 2, wherein joint body 1 can be, for example, a joint head/joint socket and joint body 2, for example, a joint socket/joint head. Thus, the contact line $k_1$ is correlated with a joint body 1 and contact line $k_2$, to a joint body 2. As can be seen from FIG. 1, the two contact lines $k_1$ and $k_2$ touch in a contact point K, if the two joint parts, that is, joint body 1 and 2, are arranged in pairs in a joint. A tangent t common to the two contact lines in contact point K runs through contact point K. As can be seen from FIG. 2, axes $m_1$ and $m_2$, which intersect at an intersection point S, run through the centers $M_1$ and $M_2$, vertical to the plane of the contact circles. This is produced, as a result of the arrangement of the planes of the contact circles, in such a way that an obtuse angle is formed between these contact circles. In the case that the angle lying between the planes of the contact circles is 180° C., the axes $m_1$ and $m_2$ intersect at infinity. A connecting line between the contact point K and the intersection point S is characterized by s. The movement vector of a momentary angular velocity around a momentary axis r, which coincides with the connecting line between the center of the circle $M_1$ and the momentary contact point K, is indicated by the arrow $\Omega_1$. The movement vector of a swivel movement around the tangent t is indicated by the arrow $\Omega_2$. Furthermore, FIG. 2 shows an angle β, which is the complementary angle to the angle enclosed between the two planes of the contact lines. The movement vector $\Omega_1$, thus indicates that the contact lines can roll onto one another and the movement vector $\Omega_2$ indicates that a swivel movement of the contact lines around the tangent can be superimposed on this rolling movement, wherein the angular velocity of this swivel movement is the rate of change of the angle $β(\Omega_2 = dβ/dt)$.

Figure 3:
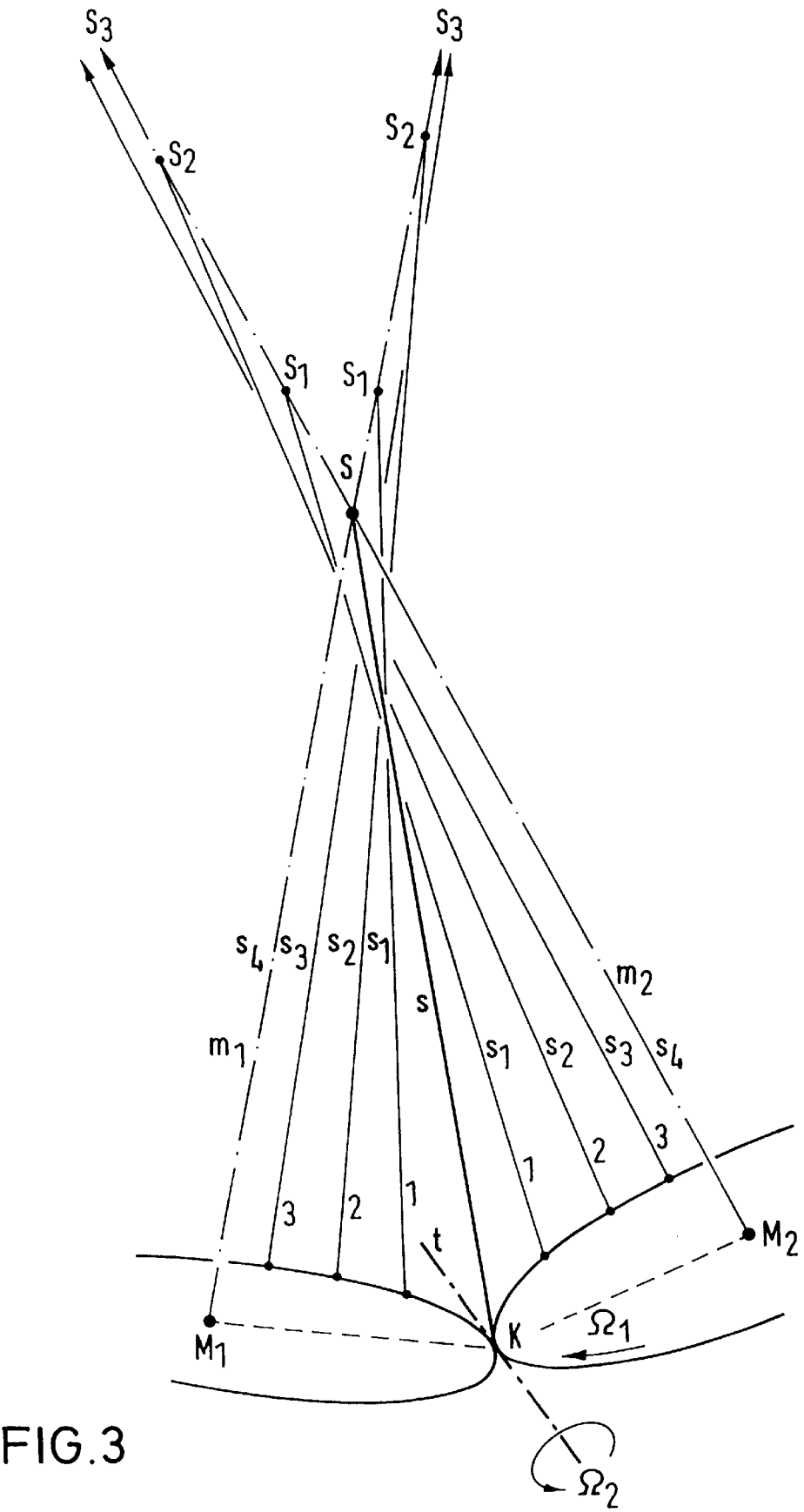
FIG. 3 shows a view according to FIG. 1 with the rolling of the contact lines, taking into consideration a swivel movement around the individual tangent t with resulting joint surfaces.

FIG. 3 shows how the intersection point S, in accordance with FIG. 2, and the connecting line s are shifted with a rolling movement of the contact lines $k_1$ and $k_2$ with a simultaneous execution of a swivel movement around the tangent t. In accordance with FIG. 3, the intersection point S of the axes $m_1$ and $m_2$ is determined at any momentary position of the contact line $k_2$. Since the contact line $k_2$ swivels, the intersection point S migrates with the movement both along the axis $m_1$ as well as the axis $m_2$. In every position, the intersection point S is connected with the momentary contact point K. The corresponding line s is the momentary pathline of contact of the two articulation surfaces, wherein the ruled surfaces 3 and 4, which join the contact lines $k_1$ and $k_2$ at one side, are formed by the totality of the contact s (sum of the pathlines of lines $S_1$, $S_2$, $S_3$...) with respect to the moved and to the unmoved contact circle or contact lines $k_1$ and $k_2$. Here, we are dealing with straight pathlines of contact s, which depict the areas of a line-shaped force transfer between the ruled surfaces 3 and 4, formed during the reciprocal articulation.

For the production of ruled surfaces 3 and 4 by means of, for example, a computer-controlled milling machine, it is possible to input the following mathematical conditions:

The two angular velocities $\Omega_1$ and $\Omega_2$ are vectors whose directions coincide with the direction of the momentary axis r or t. In vector notation, this means that:

$$\Omega_1 = \Omega_{10} \cdot (e_x \cdot \cos α + e_y \cdot \sin α),$$

and $$\Omega_2 = \Omega_{20} \cdot (e_x \cdot \sin α - e_y \cdot \cos α)$$

since $\Omega_1$ and $\Omega_2$ are vertical to one another.

$e_x$ = the unit vector in the x direction, and
$e_y$ = the unit vector in the y direction of the stationary coordinate system, in which the circle $k_1$ rests.

The following conditions should also be introduced:

$$\Omega_{10} = \Omega_0 \cdot \cos(α+δ) \text{ and } \Omega_{20} = \Omega_0 \cdot \sin(α+δ),$$

which is equivalent with the following relationship:

$$\Omega_{10}/\Omega_{20} = \cot(α+δ)$$

The introduction of this condition is possible, since the momentary rotation around the axis t can take place, in principle, independent of the momentary rotation around the axis r.

The resulting momentary angular velocity component $\Omega$ (parallel to the y-x plane) of a circular disk-like line $k_2$ is composed by means of the vector addition of the angular velocities $\Omega_1$ and $\Omega_2$.

In this way, the following is valid for $\Omega$:

$$\Omega = \Omega_0 \cdot (e_x \cdot \cos δ + e_y \cdot \sin δ),$$

which means that $\Omega$ exhibits a constant direction in the y-x plane. $\Omega_0$ can be freely selected. $\Omega_0$ specifies how rapidly the angle α changes.

By selecting the following variables:
initial value of β,
phase angle δ, and
the radii $R_1$ and $R_2$ of the circle-like lines $k_1$ and $k_2$, the totality of the possible ruled surface pairs is established.

Figure 6:
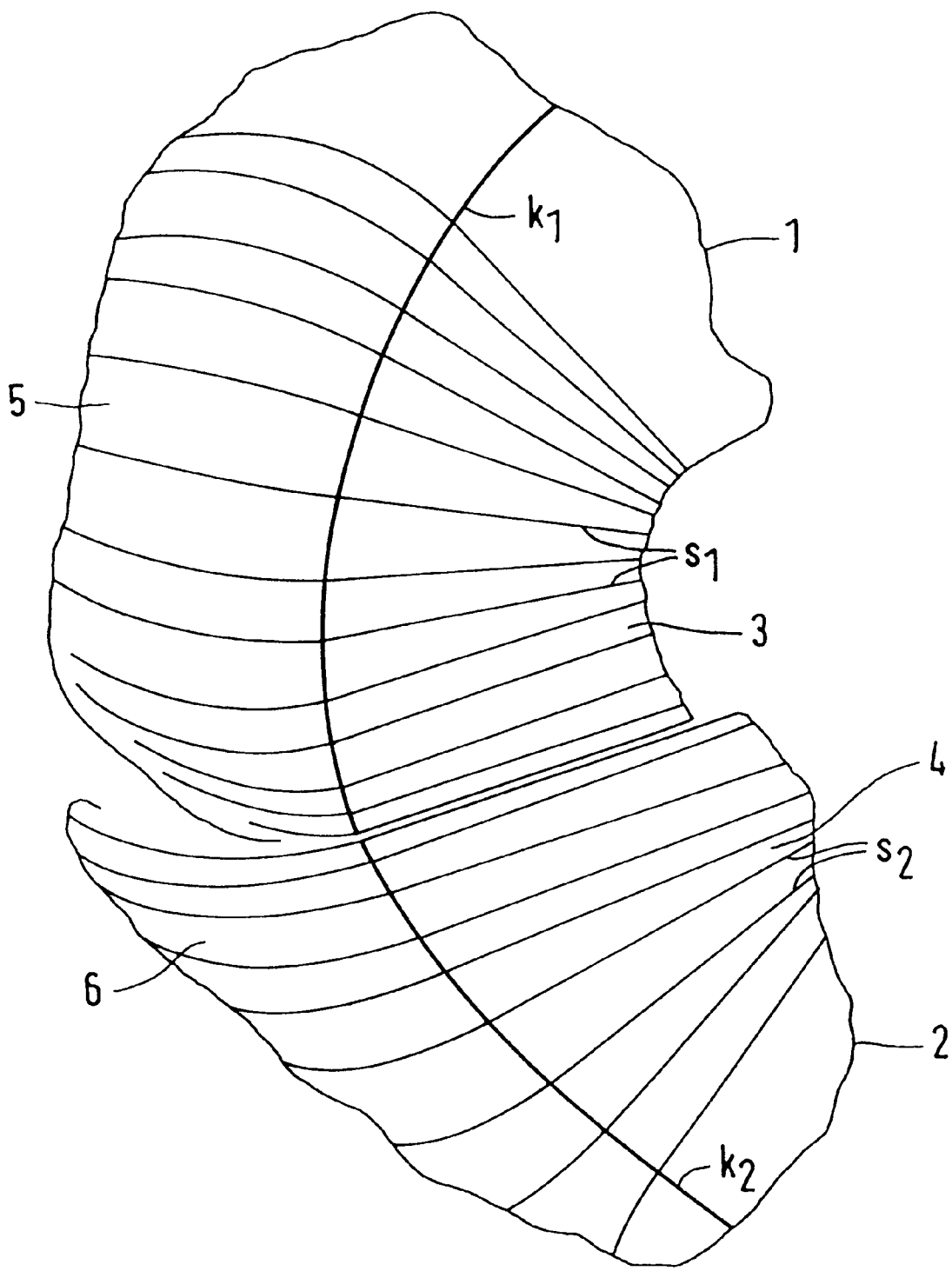
FIG. 6 shows a basic representation of the articulation surfaces in accordance with the invention.

FIG. 6 shows, in perspective view, how the articulation surface of a joint body 1 and a joint body 2 can be formed by means of the contact lines $k_1$ and $k_2$ and the ruled surfaces 3 and 4, formed from a large number of the pathlines of contact s.

Figure 4:
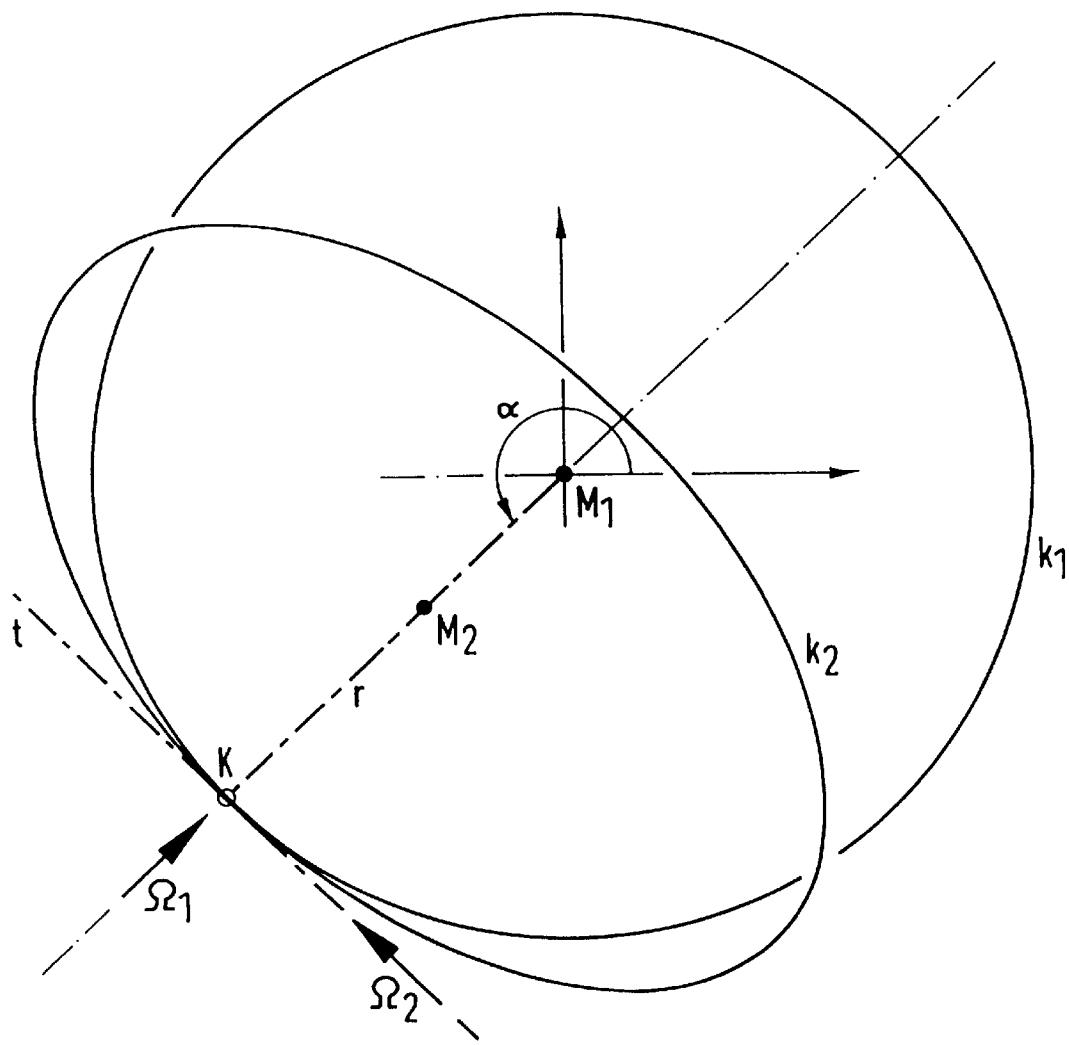
FIGS. 4 and 5 show a basic representation according to FIGS. 1 and 2; an alternative correlation of the contact circles with accompanying contact lines.
Figure 5:
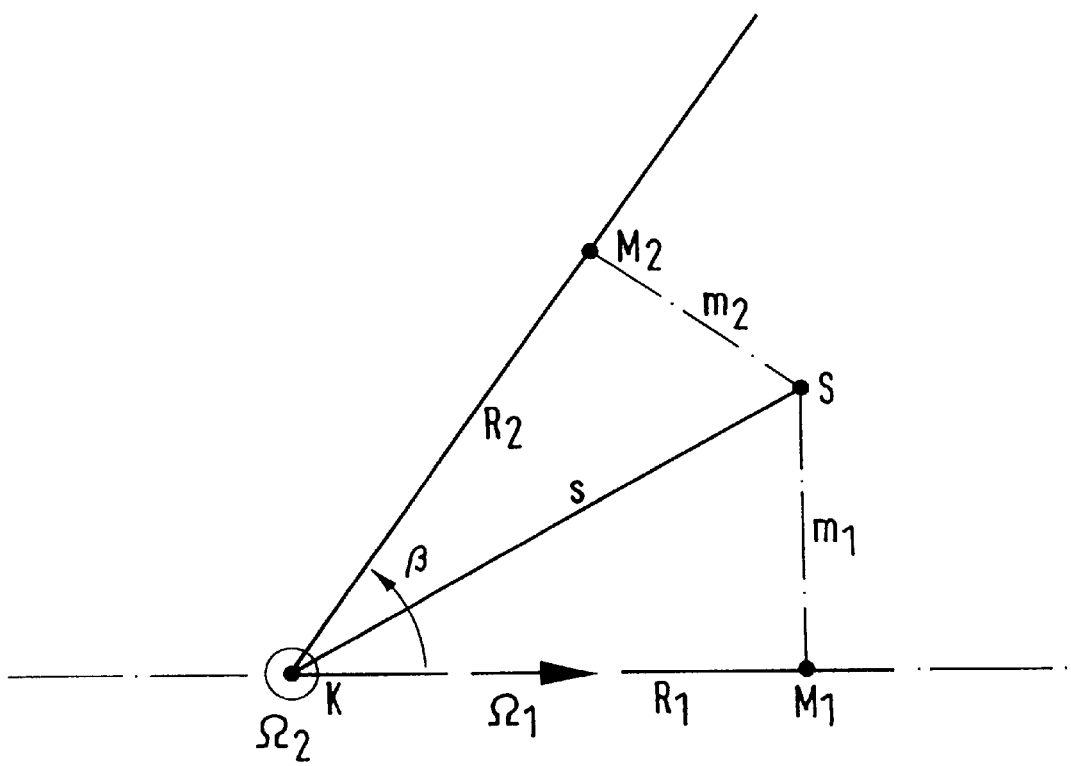

FIGS. 4 and 5 depict the same functional elements and parts with the same reference numbers as in FIGS. 1–3, wherein an alternative arrangement of the contact lines $k_1$ and $k_2$ is selected. Here the contact circles exhibiting the contact lines $k_1$ and $k_2$ are arranged with respect to one another in such a way that they enclose an acute angle between them. This means that the two contact lines $k_1$ and $k_2$ do not touch one another from the outside, that is, in a convex-convex position, but rather from the inside, that is, in a position of a concavity with a convexity, wherein, in the embodiment example shown, the contact circle $K_1$ forms the concavity and the contact circle $K_2$, the convexity.

Furthermore, as follows from FIG. 6, there is another configuration of the invention in that on the side of the contact lines $k_1$, $k_2$ opposite the ruled surfaces 3 and 4, the pathlines of contact s for the contact lines $k_1$, $k_1$ are extended outwards, advantageously in the shape of the arc of a circle, so that rolls 5,6 are formed on the joints 1,2. The rolls 5,6 are thereby formed in such a way that they do not touch during the articulation of joint body 1, 2. Furthermore, the rolls 5,6 are formed in such a manner that between them they enclose a cross-sectional area over the entire articulation area, which, in its size and form, is approximately constant. The rolls 5,6 form areas of indirect force transfer. In the gap between the rolls 5,6, tissue can be inserted laterally, which, for example, can exert a function similar to that of the menisci in the natural knee joint. Since the cross-sectional area between the rolls 5,6 is approximately constant in accordance with the invention, crushing of the inserted tissue is not produced. The center of the circle of the extensions of the pathlines of contact s, forming the roll surfaces and having the shape of the arc of a circle, is smaller than/the same as the radius of the contact circles of the contact lines.

Figure 7:
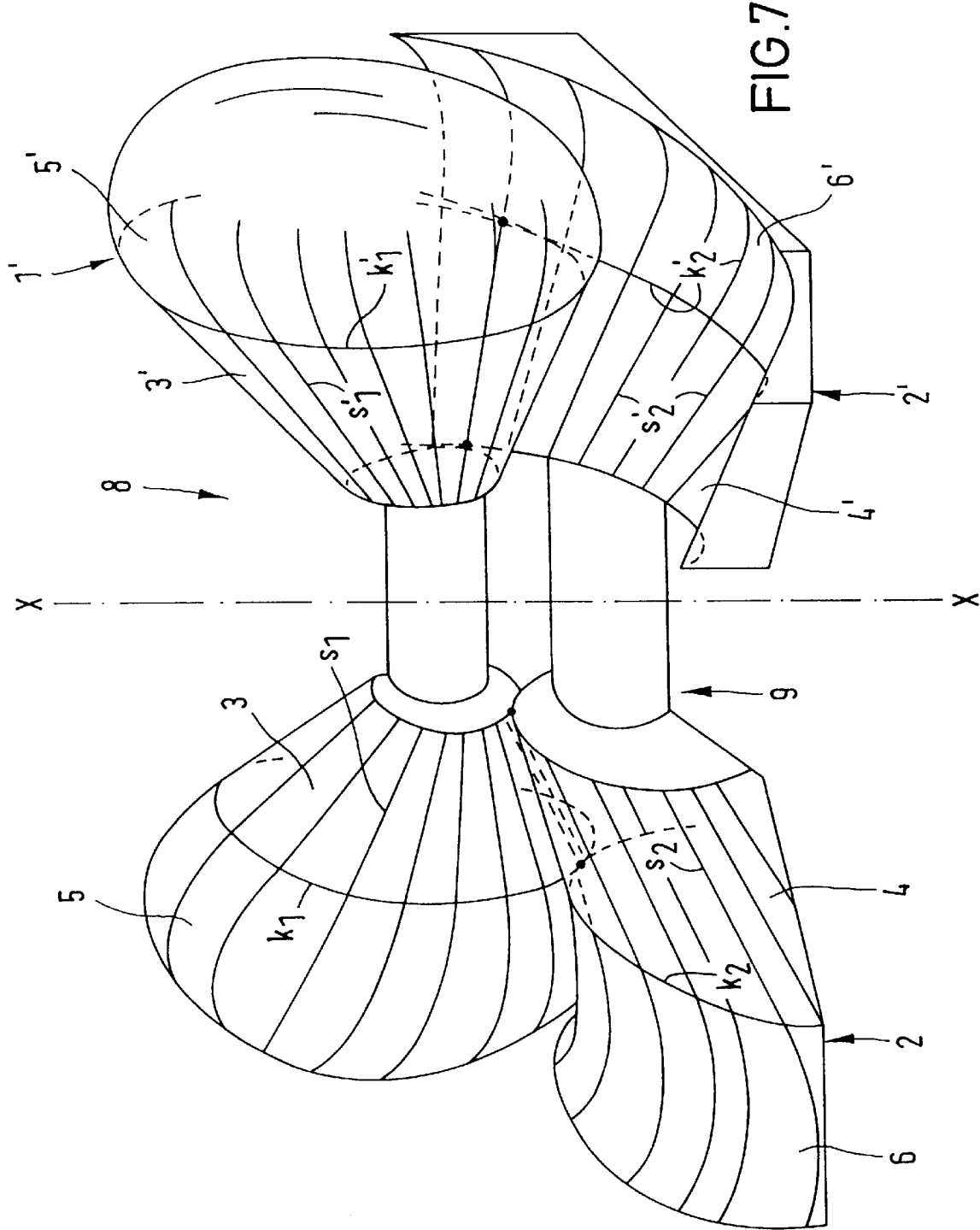
FIG. 7 shows a view of an artificial joint in accordance with the invention, as endoprosthesis for a human knee joint.

As shown in FIG. 7, the artificial joint depicted there, in accordance with the invention, can be formed as an endoprosthesis for the replacement of the human knee joint (right knee in the view from the front) from the parallel connection of two joint body pairs in accordance with the invention, 1,2; 1',2'. Here, the ruled surfaces 3,4; 3',4' of each joint body pair are arranged in such a way with respect to the middle plane X—X that they are arranged on the side facing away from the middle plane X—X. The joint body pairs 1,2; 1',2' are hereby arranged in such a way that joint body 1 and joint body 1' are rigidly connected with one another and jointly form the femoral joint head 8. Joint body 2 and joint body 2' are also rigidly connected with one another and jointly form the tibial joint body 9 (tibial joint socket) of the artificial knee joint in accordance with the invention, to replace the right knee joint. The femoral joint body 1 and the tibial joint body 2 are hereby laterally arranged and the femoral joint body 1' and the tibial joint body 2' are medially arranged. Here, it is particularly advantageous if the ruled surfaces 3, 4 or 3',4' run downwards toward the outside of the joint, that is, inclined in the tibial direction, so that any wear particles can flow, in this way, from the interior of the joint to the outside and, by means of this roof-like arrangement, the ab- or adduction stability is increased. Furthermore, it is expedient if the surfaces of the rolls 5,6 or 5',6', that is, the indirect force transfer surfaces, are situated in such a manner that an outflow of the joint wear particles is further promoted.

The parallel connection in accordance with the invention makes it possible for the limbs affixed on the femoral joint head 8 or on the tibial joint socket 9 to move linearly in an arranged functional plane. The contact line arrangement $K_1$, $K_2$ of the lateral joint hereby forms a stretched dimeric chain, and the contact line arrangement $K_1'$, $K_2^{1'}$ of the medial joint forms a crossed dimeric chain—see FIG. 4.

Figure 8:
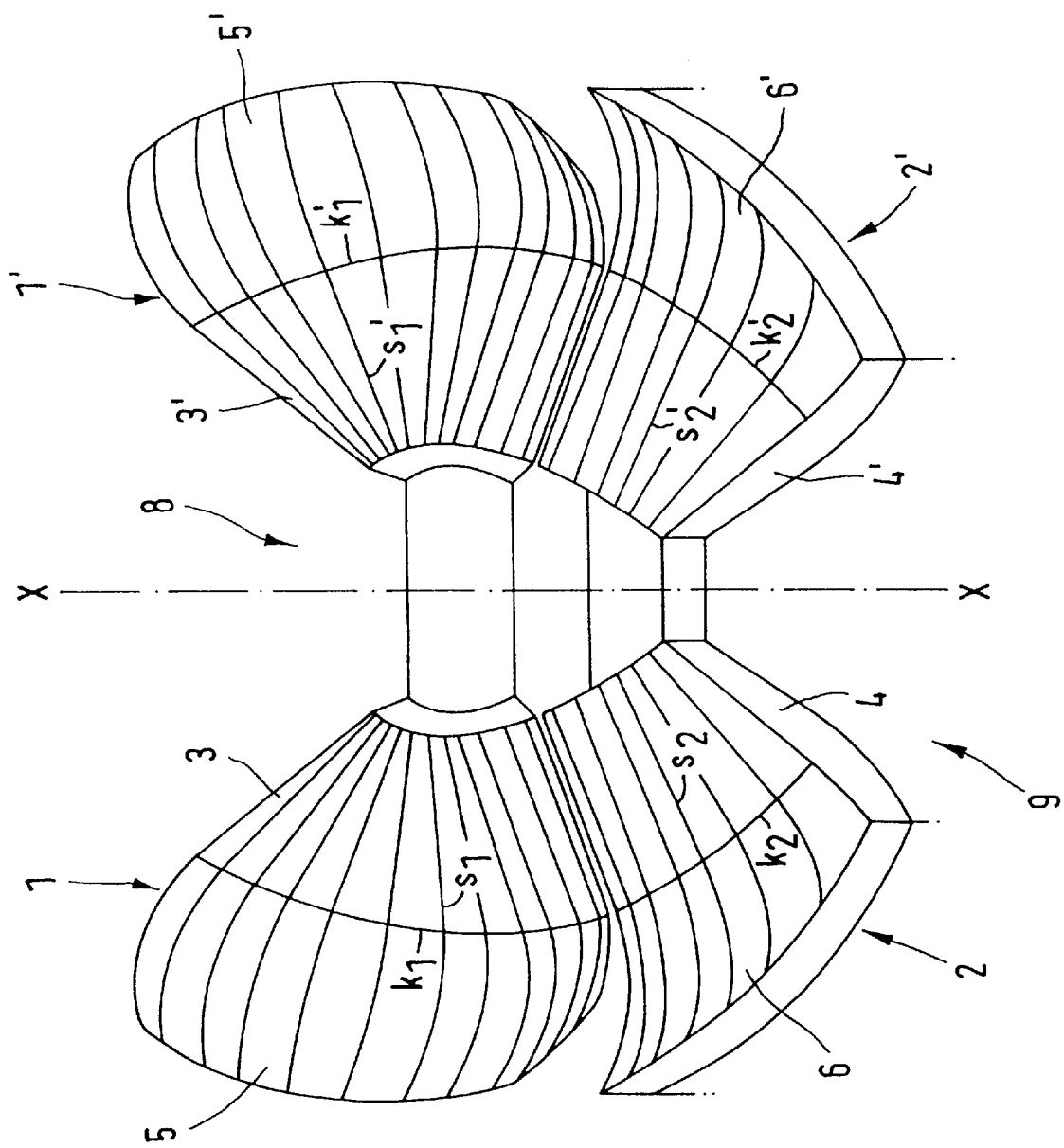
FIG. 8 shows a knee joint for four-legged animals.

FIG. 8 shows a configuration of a joint in accordance with the invention as a knee joint of a four-legged animal. Here, an execution is produced as explained in FIG. 7. However, there is a difference with respect to the execution according to FIG. 7 in that both the contact line arrangement $K_1$, $K_2$ as well as the contact line arrangement $K_1'$, $K_2'$ form a stretched dimeric chain—see FIG. 3.

The present invention is not limited to the embodiment examples shown, but rather comprises all means with the same effect in the sense of the invention.

We claim:

1. A prosthetic joint adapted to replace a natural joint comprising at least two prosthetic joint parts with curved articulation surfaces, wherein on each of the articulation surfaces is defined a contact line (k) along a circle having a center (M) and lying in a plane, wherein the articulation surfaces are arranged as a pair with respect to one another in such a manner that the contact lines (k) can roll onto one another, axes (m) running vertical to the planes and through the centers (M) of the contact circles intersect in an intersection point (S), wherein the articulation surfaces comprise ruled surfaces (3,4) which are formed from a large number of straight pathlines of contact (s) formed at one side of the contact lines (k), wherein the pathlines of contact lie on momentary connecting lines (s) extending between momentary contact points (K), appearing during the rolling movement, and the momentary intersection points (S), which are generated by a swivel movement of the contact lines (k) at an angular velocity ($\Omega$) around a common tangent (t) of the contact lines (k) through the momentary contact points (K).

2. Prosthetic joint according to claim 1, characterized in that the planes of the contact circles enclose between them an obtuse or an acute angle.

3. Prosthetic joint according to claim 1, characterized in that on the side of the contact lines (k) opposite the ruled surfaces (3,4) the pathlines of contact (s) are extended in such a way that rolls (5,6) are formed, wherein the opposing rolls (5,6) of the accompanying articulation surfaces do not have any points of contact and the cross-sectional areas which exist between them are essentially constant in size and shape in the entire articulation area.

4. Prosthetic joint according to claim 1, characterized in that the ruled surfaces (3,4) are inclined in such a way that constant outflow of wear particles takes place.

5. Prosthetic joint according to claim 1, characterized in that two joint pairs are arranged parallel to one another and jointly form an endoprosthesis for a human knee.

* * * * *